US00PP30656P2

(12) United States Plant Patent
Dragt

(10) Patent No.: US PP30,656 P2
(45) Date of Patent: Jul. 2, 2019

(54) ***HEUCHERELLA* PLANT NAMED 'HEUPIRE030'**

(50) Latin Name: **x *Heucherella***
Varietal Denomination: HEUPIRE030

(71) Applicant: Joke Dragt, Zuidwolde (NL)

(72) Inventor: Joke Dragt, Zuidwolde (NL)

(73) Assignee: AB Kwekersrechten B.V., Zuidwolde (NL)

( * ) Notice: Subject to any disclaimer, the term of this patent is extended or adjusted under 35 U.S.C. 154(b) by 0 days.

(21) Appl. No.: 15/732,942

(22) Filed: Jan. 12, 2018

(51) Int. Cl.
*A01H 5/02* (2018.01)

(52) U.S. Cl.
USPC ..... Plt./441

(58) Field of Classification Search
USPC ..... Plt./441
CPC ..... A01H 5/00; A01H 6/00; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Heucherella* plant named 'HEUPIRE030', characterized by its upright and uniformly mounded plant habit; vigorous growth habit; green and greyed green-colored leaves; early and freely flowering habit; red purple-colored flowers held above the foliar plane on dark brown-colored peduncles; resistance to Powdery Mildew; and good garden performance and winter hardiness.

2 Drawing Sheets

Botanical designation: x *Heucherella.*
Cultivar denomination: 'HEUPIRE030'.

BACKGROUND OF THE INVENTION

The present invention relates to a new and distinct *Heucherella* plant, botanically known as x *Heucherella* and hereinafter referred to by the name 'HEUPIRE030'.

The new *Heucherella* is a product of a planned breeding program conducted by the Inventor in Zuidwolde, The Netherlands. The objective of the breeding program is to create new long-flowering *Heucherella* plants that are winter hardy.

The new *Heucherella* plant originated from a cross-pollination conducted by the Inventor in Zuidwolde, The Netherlands of a proprietary selection of *Heuchera sanguine* identified as code number 083-0063, not patented, as the female, or seed, parent with *Tiarella* hybrid 'Pink Skyrocket', disclosed in U.S. Plant Pat. No. 13,382 as the male, or pollen, parent. The new *Heucherella* plant was discovered and selected by the Inventor as a single flowering plant within the progeny of the stated cross-pollination in a controlled greenhouse environment in Zuidwolde, The Netherlands in May, 2015.

Asexual reproduction of the new *Heucherella* plant by in vitro meristem culture in a controlled greenhouse environment in Zuidwolde, The Netherlands since September, 2016 has shown that the unique features of this new *Heucherella* plant are stable and reproduced true to type in successive generations.

SUMMARY OF THE INVENTION

The new *Heucherella* plant has not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HEUPIRE030'. These characteristics in combination distinguish 'HEUPIRE030' as a new and distinct *Heucherella* plant:

1. Upright and uniformly mounded plant habit.
2. Vigorous growth habit.
3. Green and greyed green-colored leaves.
4. Early and freely flowering habit.
5. Red purple-colored flowers held above the foliar plane on dark brown-colored peduncles.
6. Resistance to Powdery Mildew.
7. Good garden performance and winter hardiness.

Plants of the new *Heucherella* differ primarily from plants of the female parent selection in flower color as plants of the female parent selection have red-colored flowers.

Plants of the new *Heucherella* differ primarily from plants of the male parent, 'Pink Skyrocket', in flower color as plants of 'Pink Skyrocket' have pink and white-colored flowers.

Plants of the new *Heucherella* can be compared to plants of x *Heucherella* 'Dayglow Pink', disclosed in U.S. Plant Pat. No. 12,164. In side-by-side comparisons, plants of the new *Heucherella* differ primarily from plants of 'Dayglow Pink' in flower size and color as plants of 'Dayglow Pink' have smaller mauve pink-colored flowers. In addition, plants of the new *Heucherella* and 'Dayglow Pink' differ in leaf appearance as leaves of plants of the new *Heucherella* have a more distinct pattern than leaves of 'Dayglow Pink'.

BRIEF DESCRIPTION OF THE PHOTOGRAPHS

The accompanying colored photographs illustrate the overall appearance of the new *Heucherella* plant showing the colors as true as it is reasonably possible to obtain in colored reproductions of this type. Colors in the photographs may differ slightly from the color values cited in the detailed botanical description which accurately describe the colors of the new *Heucherella* plant.

The photograph on the first sheet is a side perspective view of a typical plant of 'HEUPIRE030' grown in a container.

The photographs at the top of the second sheet are close-up views of typical inflorescences of 'HEUPIRE030'.

The photograph at the bottom of the second sheet is a close-up view of typical leaves of 'HEUPIRE030'.

DETAILED BOTANICAL DESCRIPTION

The aforementioned photograph and following observations, measurements and values describe plants grown during the spring in 1.5-liter containers in an outdoor nursery in Zuidwolde, The Netherlands and under cultural practices typical of commercial *Heucherella* production. During the production of the plants, day temperatures ranged from 15° C. to 32° C. and night temperatures ranged from 6° C. to 20° C. Plants were one year old when the photographs and the description were taken. In the following description, color references are made to The Royal Horticultural Society Colour Chart, 2015 Edition, except where general terms of ordinary dictionary significance are used.

Botanical classification: x *Heucherella* 'HEUPIRE030'.

Parentage:

- *Female, or seed, parent.*—*Heuchera sanguine* identified as code number 083-0063, not patented.
- *Male, or pollen, parent.*—*Tiarella* hybrid 'Pink Skyrocket', disclosed in U.S. Plant Pat. No. 13,382.

Propagation:

- *Type*.—By in vitro meristem culture.
- *Time to initiate roots, summer*.—About 15 days at temperatures about 20° C.
- *Time to initiate roots, winter*.—About 20 days at temperatures about 10° C.
- *Time to produce a rooted young plant, summer*.—About 60 days at temperatures about 20° C.
- *Time to produce a rooted young plant, winter*.—About 70 days at temperatures about 15° C.
- *Root description*.—Medium in thickness, fibrous; typically creamy white in color, actual color of the roots is dependent on substrate composition, water quality, fertilizer type and formulation, substrate temperature and physiological age of roots.
- *Rooting habit*.—Moderately freely branching; medium density.

Plant description:

- *Plant and growth habit*.—Herbaceous perennial; basal rosette plant habit with leaves developing from the base; upright and uniformly mounded plant habit; overall shape, flatten globular with inflorescences held above the foliar plane; vigorous growth habit; moderate growth rate.
- *Plant height, soil level to top of foliar plane*.—About 17.5 cm.
- *Plant height, soil level to top of floral plane*.—About 57.2 cm.
- *Plant diameter or spread*.—About 73 cm.

Leaf description:

- *Arrangement*.—Leaves arranged in basal rosettes; simple.
- *Length*.—About 10.3 cm.
- *Width*.—About 10.1 cm.
- *Shape*.—Broadly ovate; palmately lobed with three to five lobes per leaf; sinuses shallow to medium in depth and divergent.
- *Apex*.—Broadly and bluntly acute.
- *Base*.—Hastate, not imbricate.
- *Margin*.—Crenate; undulate.
- *Texture and luster, upper and lower surfaces*.—Sparsely pubescent; matte.
- *Venation pattern*.—Palmate.
- *Color*.—Developing leaves, upper surface: Darker than 143A; areas surrounding main veins, close to 200A. Developing leaves, lower surface: Close to 147B. Fully expanded leaves, upper surface: Close to 137A to 137B; interveinal areas, close to 191A; areas surrounding main veins, darker than 147A; venation, close to 138A. Fully expanded leaves, lower surface: Close to between 138B and 147B; venation, close to 144B.
- *Petioles*.—Length: About 13.2 cm. Diameter: About 2 mm. Strength: Low, flexible. Texture and luster, upper and lower surfaces: Pubescent; glossy. Color, upper surface: Close to 146B and 197A. Color, lower surface: Close to 146B to 146C.

Flower description:

- *Flower type and flowering habit*.—Single campanulate flowers arranged on axillary compound racemes; freely flowering habit, about 220 flowers per raceme and about 3,000 flowers develop per plant during the flowering season; flowers face mostly outwardly.
- *Fragrance*.—Faintly fragrant; sweet, acidic.
- *Time of flowering*.—Long flowering period, plants begin flowering in the spring flower continuously until the autumn in The Netherlands; plants begin flowering about twelve weeks after planting.
- *Flower longevity*.—Individual flowers last about one week on the plant; flowers not persistent.
- *Inflorescence length*.—About 33.9 cm.
- *Inflorescence width*.—About 9.7 cm.
- *Flower diameter*.—About 9 mm.
- *Flower depth (height)*.—About 6 mm.
- *Flower buds*.—Height: About 4 mm. Diameter: About 2 mm. Shape: Obovate. Texture and luster: Smooth, glabrous; matte. Color: Close to 58B.
- *Petals*.—Quantity and arrangement: Five petals in a single whorl. Length: About 4 mm. Width: About 1 mm. Shape: Oblanceolate. Apex: Acute. Margin: Entire. Texture and luster, upper and lower surfaces: Smooth, glabrous; matte. Color: When opening, upper surface: Close to 73C to 73D. When opening, lower surface: Close to 73D. Fully opened, upper and lower surfaces: Lighter than 73D.
- *Sepals*.—Quantity and arrangement: Five sepals, fused. Length: About 6 mm. Width: About 1.5 mm. Shape: Roughly oblong. Apex: Acute. Margin: Entire. Texture and luster, upper surface: Smooth, glabrous; matte. Texture and luster, lower surface: Smooth, glabrous; slightly glossy. Color: When opening, upper and lower surfaces: Close to 68A. Fully opened, upper and lower surfaces: Close to 68B.
- *Peduncles*.—Length: About 52.2 cm. Diameter: About 2.5 mm. Strength: Moderately strong. Aspect, primary peduncles: About 25° from vertical. Aspect, lateral peduncles: About 45° from vertical. Texture and luster: Densely pubescent; moderately glossy. Color: Close to between 200A and N200A.

*Pedicels*.—Length: About 4 mm. Diameter: About 0.5 mm. Strength: Moderately strong. Aspect: About 30° from peduncle axis. Texture and luster: Moderately to densely pubescent; moderately glossy. Color: Close to 185B.

*Reproductive organs*.—Androecium: Stamen number: Ten per flower. Filament length: About 2 mm. Filament color: Close to 69D. Anther length: About 0.3 mm. Anther shape: Deltoid. Anther color: Close to 4C. Amount of pollen: None observed. Gynoecium: Pistil number: Two per flower. Pistil length: About 4 mm. Style length: About 3.75 mm. Style color: Close to N155D; proximally, close to 155A. Stigma diameter: About 0.2 mm. Stigma shape: Club-shaped. Stigma color: Close to NN155D. Ovary color: Close to 155A.

*Seeds and fruits*.—Seed and fruit production has not been observed on plants of the new *Heucherella*; flowers are sterile.

Pathogen & pest resistance: Plants of the new *Heucherella* have been observed to be relatively resistant to Powdery Mildew (*Sphaerotheca macularis*). Resistance to pests and other pathogens has not been observed on plants of the new *Heuchera* grown under commercial conditions to date.

Garden performance: Plants of the new *Heucherella* have been observed to have good garden performance and to tolerate high temperatures about 35° C. and to be suitable for USDA Hardiness Zones 3 through 9.

It is claimed:

1. A new and distinct *Heucherella* plant named 'HEUPIRE030' as illustrated and described.

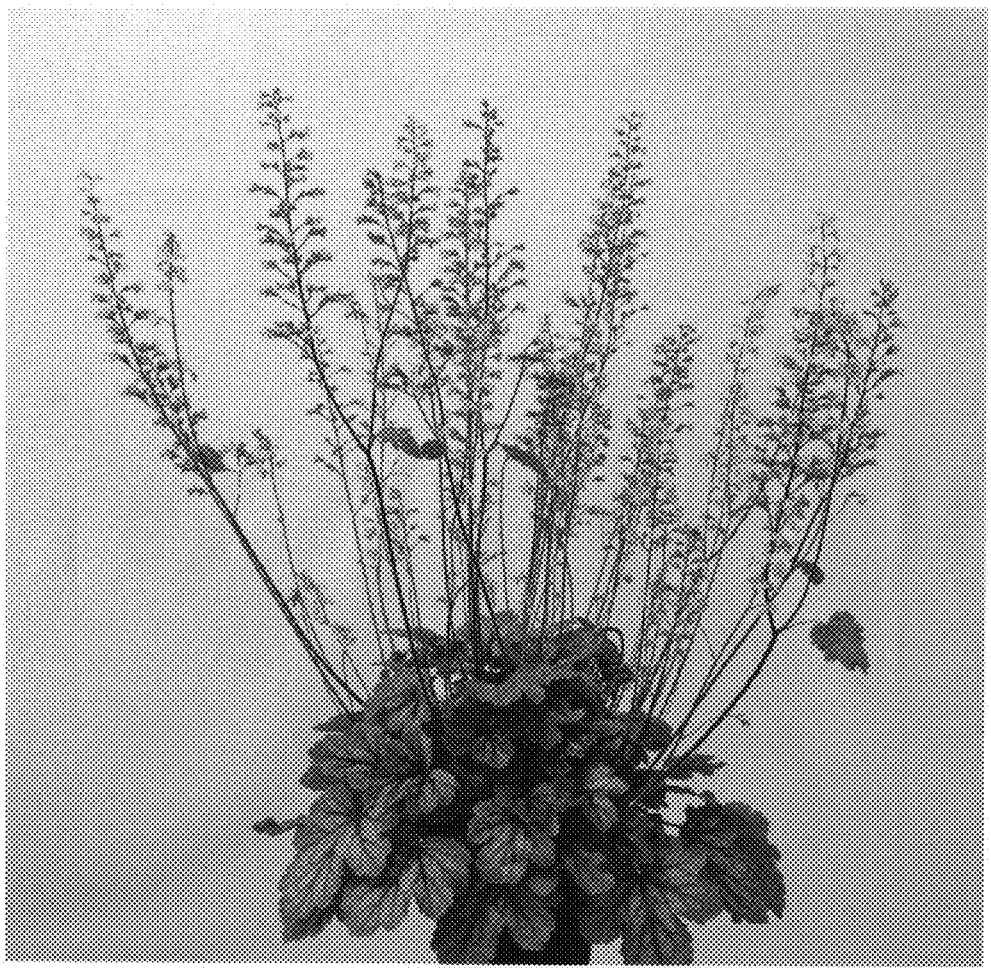

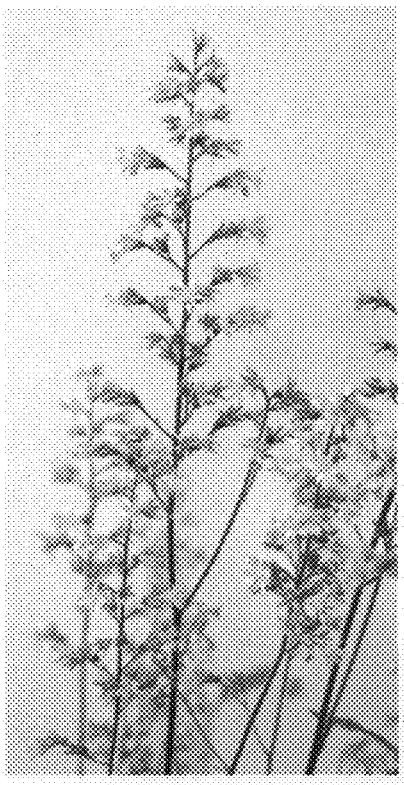
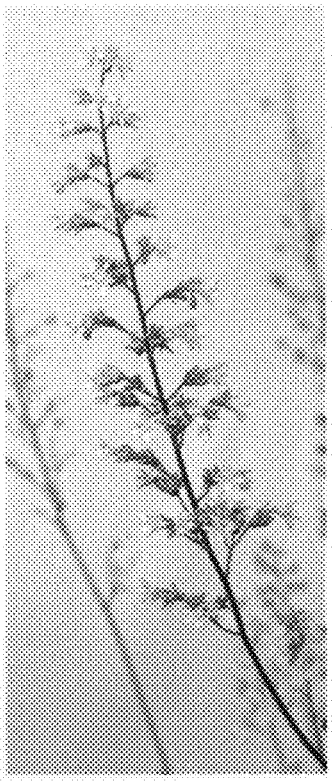
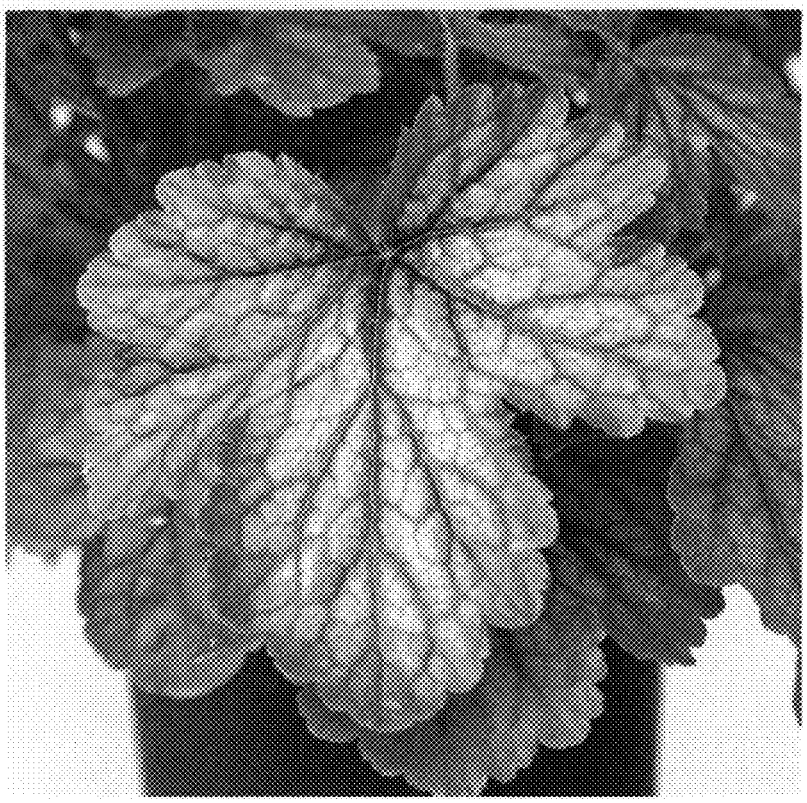

* * * * *